US011745184B1

(12) United States Patent
Rabbani

(10) Patent No.: US 11,745,184 B1

(45) Date of Patent: Sep. 5, 2023

(54) REDUCED BACKGROUND IMMUNOASSAY PLATES

(71) Applicant: Enzo Biochem, Inc., New York, NY (US)

(72) Inventor: Elazar Rabbani, New York, NY (US)

( * ) Notice: Subject to any disclaimer, the term of this patent is extended or adjusted under 35 U.S.C. 154(b) by 246 days.

(21) Appl. No.: 17/352,424

(22) Filed: Jun. 21, 2021

Related U.S. Application Data

(62) Division of application No. 16/260,232, filed on Jan. 29, 2019, now abandoned.

(60) Provisional application No. 62/639,340, filed on Mar. 6, 2018.

(51) Int. Cl.
*B01L 3/00* (2006.01)
*C12M 1/32* (2006.01)

(52) U.S. Cl.
CPC .......... *B01L 3/5085* (2013.01); *C12M 23/12* (2013.01); *B01L 2300/0829* (2013.01); *B01L 2300/163* (2013.01); *B01L 2300/165* (2013.01); *B01L 2300/168* (2013.01)

(58) Field of Classification Search
CPC .......... B01L 3/5085; B01L 2300/0829; B01L 2300/163; B01L 2300/165; B01L 2300/168; C12M 23/12
See application file for complete search history.

(56) References Cited

U.S. PATENT DOCUMENTS 6,093,559 A 7/2000 Bookbinder et al.
2014/0220606 A1 8/2014 Puntambekar
2018/0326412 A1 11/2018 Rothberg

FOREIGN PATENT DOCUMENTS

AU 2008/229944 11/2008

OTHER PUBLICATIONS

Enzo Product Manual, IL-6 (human), high sensitivitv ELISA Kit, Catalog #: ENZ-KIT178-0001, 96-Weil Kit, Revision Oct. 30, 2017.

*Primary Examiner* — Jennifer Wecker
*Assistant Examiner* — Kathryn Elizabeth Limbaugh

(57) ABSTRACT

The invention provides reduced background substrates, such as multi-well plates, for use in enzyme-linked immunosorbent assays (ELISAs) and other ligand-binding assays, and methods for making and using the same.

4 Claims, 2 Drawing Sheets

IL-6, Full sandwich ELISA, with background values (Enzo kit vs newly developed assay)

| | 10 pg/ml | 5 pg/ml | 2.5 pg/ml | 1.25 pg/ml | 0.625 pg/ml | 0.312 pg/ml | 0.156 pg/ml | Blank |
|---|---|---|---|---|---|---|---|---|
| Enzo IL-6 Kit | 0.214 | 0.146 | 0.098 | 0.052 | 0.043 | 0.045 | 0.044 | 0.043 |
| PG coating + 10 µl chloroform | 0.251 | 0.218 | 0.179 | 0.143 | 0.112 | 0.089 | 0.068 | 0.029 |

Enzo IL-6 Kit   PG coating + 10 µl chloroform

REDUCED BACKGROUND IMMUNOASSAY PLATES

CROSS-REFERENCE TO RELATED APPLICATIONS

This application is a divisional of U.S. application Ser. No. 16/260,232 filed Jan. 29, 2019, which claims the benefit of U.S. provisional application Ser. No. 62/639,340 filed Mar. 6, 2018, each of which is hereby incorporated by reference in its entirety.

FIELD OF THE INVENTION

The present invention relates to the field of immunoassay substrates.

BACKGROUND OF THE INVENTION

ELISA (enzyme-linked immunosorbent assay) is a plate-based assay technique for detecting and quantifying substances such as peptides, proteins, hormones, vitamins and drug substances in a sample. In one format of ELISA, the substance of interest (or "antigen") present in a sample is indirectly immobilized to a solid surface by a capture antibody which is specific for the antigen and which is directly bound to the surface, which is typically the surface of a well of a multi-well microplate plate. A detection antibody, which is conjugated to an enzyme and also specific for the antigen, is then introduced to bind to any antigen that is immobilized by the capture antibody. After unbound detection antibody is washed away, conjugated enzyme activity is quantified by incubation with an enzyme substrate to produce a detectable product.

What is needed and provided by the present invention are reduced background substrates for performing ligand-binding assays, such as ELISAs.

SUMMARY OF THE INVENTION

One embodiment of the invention provides a composition of matter that includes:

- a walled vessel including an inner surface having an area and defining a volume, wherein the inner surface is composed of a protein-binding material, and
- wherein the inner surface is partially coated with a low protein-binding material and the remainder of the inner surface directly presents the protein-binding material to the volume.

The composition of matter may, for example, be a multi-well microplate, in which at least one of the wells of said microplate is a walled vessel as recited. Part or at least substantially all of the bottom of the vessel(s) may, for example, present the protein-binding material to the volume, while the side wall(s) are at least predominantly, such as fully, coated with the low protein-binding material.

A related embodiment of the invention provides a multi-well microplate that includes:

- a plurality of columnar wells, each including an inner surface having an area and defining a volume,
- wherein for one or more of the plurality of the columnar wells,
  - the inner surface is composed of a protein-binding material, and
  - the inner surface is partially coated with a low-protein-binding material and the remainder of the inner surface directly presents the protein-binding material to the volume.

Part or at least substantially all of the bottom of the wells may, for example, present the protein-binding material to the volume, while the side walls are at least predominantly, such as fully, coated with the low protein-binding material.

A further embodiment of the invention provides a method for making a reduced background multi-well microtiter plate for use in ligand-binding assays that includes the steps of:

- providing a multi-well microtiter plate, wherein the inner surface of at least one of the wells is protein-binding;
- coating at least part of the inner surface of the at least one of the wells that is protein-binding, such as all of the wells, with a low protein-binding coating material, such as any of those described herein; and
- removing the coating from only part of the coated surface, such as removing the coating from part or all of the bottom of the well(s) that were coated and not substantially from the side walls. The coating may be removed, for example, by adding a solvent (capable of dissolving the coating and/or disrupting the bond of the coating to the surface) to the bottom of the well, incubating for a time, and then removing the dissolved/disrupted coating, followed by optional washes.

The plate itself may be composed of a protein-binding material such as a protein-binding polymer, mixture of polymers or glass, for example, as described herein.

A related embodiment of the invention provides a method for making a reduced background multi-well microtiter plate for use in ligand-binding assays that includes the steps of:

- providing a multi-well microtiter plate, wherein said plate is composed of a protein-binding material so that the inner surface of at least some of the wells is protein-binding;
- adding a liquid including a coating material (such as any of those described herein) to at least one of the wells, such as all of the wells, to coat the bottom of the well(s) and the side wall of the wells (up to a preselected height or at least the substantially to the top) with the low protein-binding coating material;
- removing the liquid including the coating material from the well(s);
- adding a solvent (capable of dissolving the coating and/or disrupting the bond of the coating to the surface) to at least one of the coated wells to remove the coating from only part of the coated surface, such as removing the coating only from part or all of the bottom of the well(s) that were coated; and
- removing the added solvent from the well(s).

Additional features, advantages, and embodiments of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

Figure 1A:
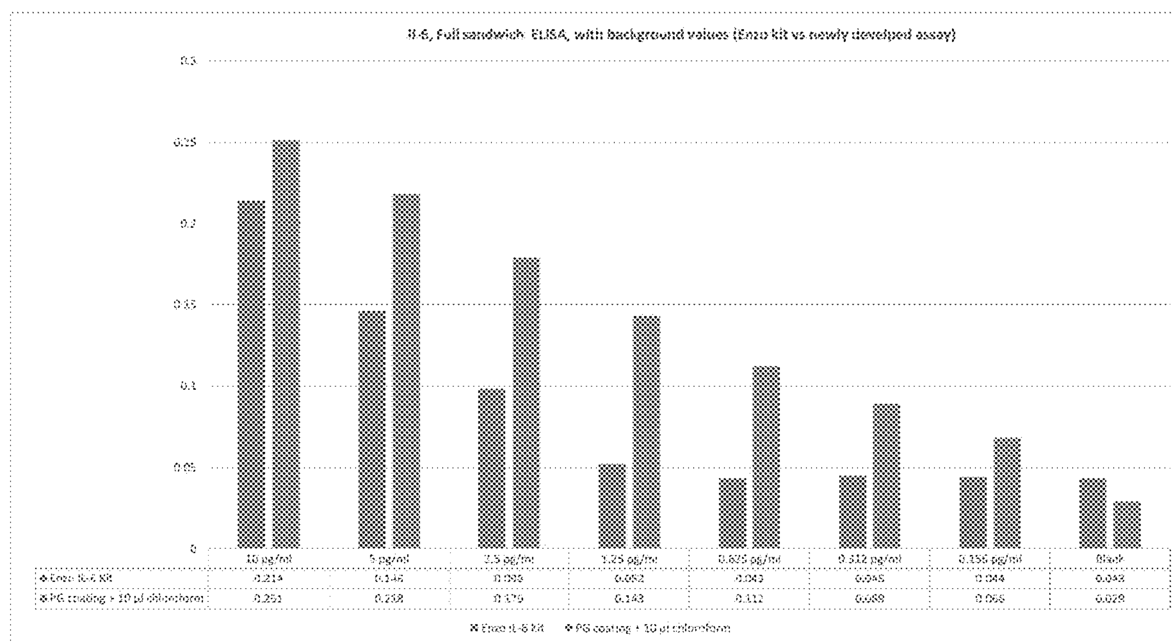
FIG. 1A shows the results of an experiment comparing the detection of different concentrations of IL-6 using an ELISA sandwich assay on a conventional multi-well immunoassay plate and a reduced background multi-well immunoassay plate embodiment of the invention.

The invention provides reduced background solid substrates, such as multi-well microplates, for use in ligand-binding assays such as but not limited to enzyme-linked immunosorbent assays (ELISAs), and methods for making and using the same.

In one aspect, the invention provides multi-well microplates in which the inner surface of wells is partially blocked to protein binding, e.g., the sidewalls are at least substantially blocked to protein binding, while the bottom surface of the wells presents a protein-binding surface. The following example illustrates the preparation of one such embodiment.

EXAMPLE

Materials and Methods:

Preparation of 0.1% Polyglycol (PG) solution for plate treatment:

Poly(ethyleneglycol)-block-poly(propyleneglycol)-block-poly(ethyleneglycol) (Sigma Cat # 435457, hereafter "Polyglycol" or "PG") nonionic surfactant 0.1% solution was prepared in 100% isopropanol and the solution was kept at room temperature.

Polyglycol (PG) coating of ELISA plates:

PG solution (0.1%, 400 μl) was added to the wells of protein-binding multi-well plates and left at room temperature overnight with a plastic film seal to prevent drying. Solution was removed from the wells and the multi-well plates were then kept (baked) at 65° C. for 2h. The wells were then washed with 400 μl of Milli Q water (18.2 MΩ.cm), emptied and inverted and tapped on paper towel to remove any residual liquid. The wash cycle was repeated 10 times before further processing or use.

Removal of PG coating to reveal protein-binding surface

15 μl of chloroform was spotted on the bottom of selected wells of fully Polyglycol coated plates. This volume was sufficient to contact the entire bottom surface of a well. After multiple rounds of washing with Milli-Q $H_2O$, plates were ready for use in ELISA assays.

The following buffer solutions were prepared for use in the experiments.

| Buffers | Working solution | Stock Solution |
|---|---|---|
| Assay Buffer (1X) | 50 mM Tris, pH 8.0<br>150 mM NaCl<br>0.1 mM $ZnSO_4$<br>4.9 mM $MgCl_2$<br>0.09% $NaN_3$<br>0.1% BSA | 10X |
| Coating Buffer (1X) | 10 mM Na Phosphate, pH 8.0<br>0.01% $NaN_3$ | 10X |
| Blocking Buffer (2X) | 20 mM Na Phosphate, pH 8.0<br>30 mM NaCl<br>2% Sucrose<br>0.02% Tween 20<br>0.4% BSA<br>0.02% $NaN_3$ | 10X |
| Wash Buffer (1X) | 50 mM Tris, pH 7.5<br>100 mM NaCl<br>0.01% Hydorol M<br>0.05% Tween 20 | 10X |

Antigen preparation:

The antigen standards run in the assay were prepared by serially diluting the stock in 1× assay buffer to 10, 5, 2.5, 1.25, 0.625, 0.312, and 0.156 pg/ml (1:2 dilutions) concentrations. Six 12×75 mm polypropylene tubes were labeled #1 through #6. 450 μL of assay buffer was added into tube #1. 250 μL of assay buffer was added into tube #2 through tube #5. Added 50 μL of 500 pg/ml IL-6 standard stock to tube #1. The tubes were mixed gently by vortexing. 250 μL of tube #1 was added into tube #2 and vortexed gently to mix. This process was continued for tubes #2 through #6.

Capture antibody plate preparation:

IL-6 capture antibody was diluted to 2 μg/ml in 1× coating buffer (20 μL Rat anti-human IL-6 Mab stock Cat # CABT WN1691; 1 mg/ml in 10 ml, 1× coating buffer). Diluted capture antibody (100 μl) was added to Polyglycol-coated, chloroform-treated wells with incubation at room temperature overnight. A 2× dilution of blocking buffer was prepared by adding 2 ml, 10× buffer per 8 ml $dH_2O$. Wells were blocked with 100 μl 2× blocking buffer with incubation at room temperature overnight. The wells were then aspirated the plates were dried at room temperature for 1-2 hr.

EXPERIMENT

In this experiment, comparisons were made between ELISA assays performed for IL-6 cytokine using the newly developed Polyglycol-coated, chloroform-treated plates and plates from a commercially available IL-6 (human), high sensitivity ELISA Kit (Cat # ENZ-KIT178-0001, Enzo Life Sciences, Inc., Farmingdale, NY), which are protein-binding, not PG-coated, and comparably prepared with IL-6 capture antibody and blocking buffer. The plates from the kit and those used to construct the embodiment are both high protein-binding polystyrene multi-well microplates. The components of the kit were used to perform the ELISA assays for both types of plates.

100 μl of standards #1 through #6 was added into the appropriate wells. On each plate, empty wells were used to prepare a control of the relative signal intensity. The plates were sealed and incubated at room temperature on a plate shaker for 1 h (~500 rpm). The contents of the wells were aspirated and the wells were washed by adding a full well volume (~400 μl) of 1× Wash Buffer to each well. The wash was repeated 3 more times for a total of 4 washes. After the final wash, the wells were aspirated and the plate was firmly tapped on a lint-free paper towel to remove any remaining wash buffer. 100 μl of 1× IL-6 antibody was then added into each well, except the blank. The plates were sealed and incubated at room temperature (RT) on a plate shaker for 1 hour at ~500 rpm. The wells were then washed as described above. 100 μl of SA-poly HRP (80 ng/ml) was added into each well (except for the blank) and incubated at room temperature without shaking for 30 minutes.

The wells were then washed as described above, TMB Peroxidase Substrate (100 μl) was added to each well and left at room temperature on a plate shaker at ~500 rpm for approximately 10-15 min, and then the reaction was stopped by adding 100 μl stop solution. Readings from each well were taken within 5 min using a plate reader with absorbance measured at 450 nm.

FIG. 1A shows the results of the experiment comparing the detection of the different concentrations of IL-6 using an ELISA sandwich assay using the conventional multi-well immunoassay plate and the reduced background multi-well immunoassay plate embodiment of the invention in which the side walls are PG-coated and the well bottoms are protein-binding.

Figure 1B:
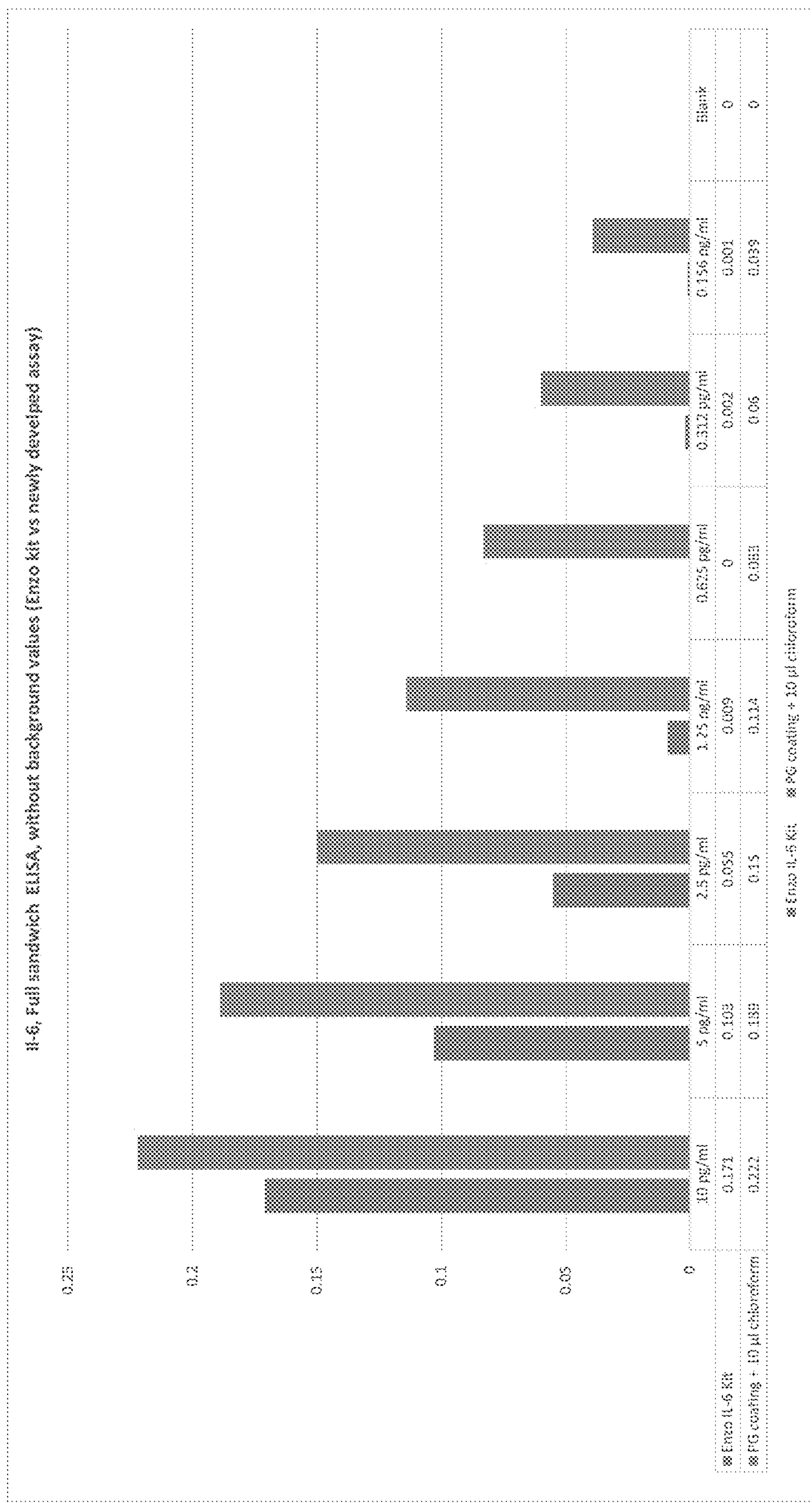
FIG. 1B presents the data shown in FIG. 1A adjusted by subtraction of the background values obtained for the conventional plate and the reduced background plate embodiment of the invention, respectively.

FIG. 1B presents the data shown in FIG. 1A adjusted by subtraction of the background values obtained for the conventional plate and the plate embodiment of the invention, respectively.

Without limitation, the invention further provides the following embodiments and variations thereof.

One embodiment of the invention provides a composition of matter that includes:

a walled vessel including an inner surface having an area and defining a volume, wherein the inner surface is composed of a protein-binding material, and wherein the inner surface is partially coated with a low protein-binding material and the remainder of the inner surface directly presents the protein-binding material to the volume.

The composition of matter may, for example, be a multi-well microplate, in which at least one of the wells of said microplate is a walled vessel as recited.

A related embodiment of the invention provides a multi-well microplate that includes:

a plurality of columnar wells, each including an inner surface having an area and defining a volume, wherein for one or more of the plurality of the columnar wells, the inner surface is composed of a protein-binding material, and the inner surface is partially coated with a low-protein-binding material and the remainder of the inner surface directly presents the protein-binding material to the volume.

The walled vessel and multi-well microplates may be transparent, for example, at least substantially entirely transparent or at least their bottom portions/walls may be transparent. Side walls may be transparent or opaque. The inner surface of the walled vessel or well(s) in the embodiments may, for example, be columnar. The inner surface may, for example, have a circular cross-sectional profile. The inner surface may, for example, have a bottom portion and a side wall portion wherein the bottom portion presents the protein-binding material to the volume and the side wall portion is at least substantially coated with and presents the low-protein-binding material to the volume. The side wall portion may have a circular cross-sectional profile. The side wall portion may, for example, be cylindrical. The bottom portion may, for example, be flat or curved, such as hemispherical. The inner surface may, for example, be composed of glass or a synthetic polymer, such as or including polystyrene, or a mixture of synthetic polymers. The glass or synthetic polymer or mixture of synthetic polymers may, for example, be protein-binding, such as high protein-binding and directly provide the protein-binding surface of the composition of matter or microplate.

In any of the embodiments herein, the low protein-binding material may, for example, include a non-ionic surfactant having a hydrophilic-lipophilic balance number (HLB number) less than or equal to 5. The low-protein-binding material may, for example, include a poloxamer. The poloxamer may, for example, have a hydrophilic-lipophilic balance number (HLB number) less than or equal to 5. The low protein-binding material may, for example, not include protein and/or not include peptides.

In one variation of the composition of matter or multi-well microplate embodiments, the inner surface has a bottom portion and a side wall portion and, for the one or more of the plurality of columnar vessels/wells, the bottom portion presents the protein-binding material to the volume and the side wall portion is at least substantially coated with and presents the low-protein-binding material to the volume.

In another variation, the composition of matter or multi-well microplate further includes an at least substantially pure antibody specific for an antigen, said antibody adsorbed to the protein binding material of the remainder of the inner surface that directly presents the protein-binding material to the volume, wherein the at least substantially pure antigen-specific antibody is at least substantially not bound to the coating of low-protein binding material of the inner surface. In a related variation, still further included is the antigen (i.e., a quantity thereof) wherein the antigen is specifically bound to at least some of said at least substantially pure antibody specific for the antigen. The antigen may, for example, include or be a peptide or a polypeptide or a small molecule.

A further embodiment of the invention provides a method for making a reduced background multi-well microtiter plate for use in ligand-binding assays that includes the steps of:

providing a multi-well microtiter plate, wherein the inner surface of at least one of the wells is protein-binding;

coating at least part of the inner surface of the at least one of the wells that is protein binding, such as all of the wells, with a low protein-binding coating material, such as any of those described herein; and removing the coating from only part of the coated surface, such as removing the coating from part or all of the bottom of the well(s) that were coated and not substantially from the side walls. The coating may be removed, for example, by adding a solvent (capable of dissolving the coating and/or disrupting the bond of the coating to the surface) to the bottom of the well, incubating for a time, and then removing the coating, followed by optional washes. The plate itself may be composed of a protein-binding material such as a protein-binding polymer, mixture of polymers or glass, for example, as described herein. The solvent may, for example, be an organic solvent such as chloroform or xylene.

A related embodiment of the invention provides a method for making a reduced background multi-well microtiter plate for use in ligand-binding assays that includes the steps of:

providing a multi-well microtiter plate, wherein said plate is composed of a protein-binding material so that the inner surface of at least some of the wells is protein-binding;

adding a liquid including a coating material (such as any of those described herein) to at least one of the wells, such as all of the wells, to coat the bottom of the well(s) and the side wall of the wells (up to a preselected height or at least the substantially to the top) with the low protein-binding coating material;

removing the liquid including the coating material from the well(s);

adding a solvent (capable of dissolving the coating and/or disrupting the bond of the coating to the surface) to at least one of the coated wells to remove the coating from only part of the coated surface, such as removing the coating only from part or all of the bottom of the well(s) that were coated; and removing the added solvent from the well(s).

The solvent may, for example, be an organic solvent such as chloroform or xylene. To remove coating from the bottom of the wells without removing a substantial amount of coating from the side walls, an amount of solvent sufficient to just cover the bottom of the wells without substantially going up the side walls may be deposited at the bottom of each treated well. The method may further comprise a heat treatment or "baking step" between removal of the liquid comprising the coating material and addition of the solvent.

While various aspects of the inventions are illustrated herein with respect to ELISA assays, it should be understood that the invention is generally applicable to ligand-binding assays performed in walled vessels such as wells of microplates. It should also be understood that wherever in this disclosure the term include(s), including, comprise(s) or comprising is recited, corresponding embodiments reciting the term consist(s) essentially of, consisting essentially of, consist(s) of, and consisting of are also provided by the invention and disclosed herein.

Any and all publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s). Moreover, features described in connection with one embodiment of the invention may be used in conjunction with other embodiments, even if not explicitly exemplified in combination within.

What is claimed is:

1. A method for making a reduced background multi-well microtiter plate for use in ligand-binding assays, comprising the steps of:

providing a multi-well microtiter plate, wherein the inner surface of at least some of the wells is protein-binding;

coating at least part of the inner surface of at least one of the wells that has a protein-binding surface with a low protein-binding coating material; and removing the coating from only part of the coated surface.

2. The method of claim 1, wherein the coating is removed from part or all of the bottom of the coated well(s) and at least predominantly not removed from the side wall of said well(s).

3. A method for making a reduced background multi-well microtiter plate for use in ligand-binding assays, comprising the steps of:

providing a multi-well microtiter plate, wherein said plate is composed of a protein-binding material so that the inner surface of at least some of the wells is protein-binding;

adding a liquid comprising a low protein-binding coating material to at least one of the wells that has a protein-binding inner surface to coat the bottom of the well(s) and the side wall of the well(s)s up to a preselected height or at least the substantially to the top with the low protein-binding coating material;

removing the liquid comprising the coating material from the well(s);

adding a solvent to at least one coated well to remove the coating from only part of the coated surface; and removing the added solvent from the well(s).

4. The method of claim 3, wherein the coating is removed from part or all of the bottom of the coated well(s) and at least predominantly not removed from the side wall of said well(s).

* * * * *